United States Patent
Truong et al.

(10) Patent No.: US 10,441,672 B2
(45) Date of Patent: *Oct. 15, 2019

(54) APPARATUS AND METHOD FOR DETECTING MOISTURE IN A VACUUM CHAMBER

(71) Applicant: ETHICON, INC., Somerville, NJ (US)

(72) Inventors: Doug Vo Truong, Irvine, CA (US); Todd Morrison, Dana Point, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 513 days.

This patent is subject to a terminal disclaimer.

(21) Appl. No.: 15/139,032

(22) Filed: Apr. 26, 2016

(65) Prior Publication Data
US 2017/0304477 A1   Oct. 26, 2017

(51) Int. Cl.
*A61L 2/24* (2006.01)
*G01N 33/18* (2006.01)
(Continued)

(52) U.S. Cl.
CPC ........ *A61L 2/24* (2013.01); *A61L 2/00* (2013.01); *A61L 2/208* (2013.01); *A61L 2/28* (2013.01); *G01N 33/18* (2013.01); *A61L 2202/14* (2013.01)

(58) Field of Classification Search
CPC .................................. A61L 2/24; A61L 2/208
See application file for complete search history.

(56) References Cited

U.S. PATENT DOCUMENTS

| 4,551,311 A | 11/1985 | Lorenz |
| 4,551,331 A | 11/1985 | Rudin |

(Continued)

FOREIGN PATENT DOCUMENTS

| DE | 102012201432 A1 | 8/2013 |
| EP | 2902042 A1 | 8/2015 |

(Continued)

OTHER PUBLICATIONS

Encyclopedia Britannica. Computer Process Control. Last text revision May 31, 2002 (Year: 2002).*

(Continued)

*Primary Examiner* — Donald R Spamer
(74) *Attorney, Agent, or Firm* — Roberts Mlotkowski Safran Cole & Calderon, P.C.

(57) ABSTRACT

A method of sterilizing medical instruments using a vacuum chamber connected to reservoir by a valve in a closed state is disclosed that includes placing instruments in a non-sterile state into a sterilization pack, opening a chamber, placing the pack into the chamber, closing the chamber, withdrawing a first volume of air from the chamber, changing a volume of liquid water into vapor, opening the valve, introducing sterilant into the chamber, introducing a second volume of air into the chamber, opening the chamber, removing the pack from the chamber, and removing the instruments in a sterile-state from the pack. The process may further include the steps of repeatedly determining pressure within the chamber, calculating second-derivative values of pressure with respect to time, and determining whether any local maxima exist in a plot of second derivative values that correspond to pressures above and/or below the triple-point pressure of water.

31 Claims, 6 Drawing Sheets

(51) Int. Cl.
*A61L 2/20* (2006.01)
*A61L 2/28* (2006.01)
*A61L 2/00* (2006.01)

(56) References Cited

U.S. PATENT DOCUMENTS

| | | |
|---|---|---|
| 4,643,876 A | 2/1987 | Jacobs et al. |
| 4,756,882 A | 7/1988 | Jacobs et al. |
| 5,317,896 A | 6/1994 | Sheth et al. |
| 5,482,683 A | 1/1996 | Sheth et al. |
| 5,641,455 A | 6/1997 | Rosenlund et al. |
| 5,788,925 A | 8/1998 | Pai et al. |
| 5,961,922 A | 10/1999 | Witte et al. |
| 8,366,995 B2 | 2/2013 | McLaren et al. |
| 9,277,850 B2 | 3/2016 | Kubach |
| 2010/0313441 A1 | 12/2010 | McLaren et al. |
| 2015/0313250 A1 | 11/2015 | Itarashiki et al. |
| 2017/0326265 A1 | 11/2017 | Chin |

FOREIGN PATENT DOCUMENTS

| | | |
|---|---|---|
| WO | 2007012866 A1 | 2/2007 |
| WO | 2007125100 A1 | 11/2007 |
| WO | 2008134290 A1 | 11/2008 |

OTHER PUBLICATIONS

Rutala et al. Guidline for Disinfection and Sterilization in Healthcare Facilities. Center for Disease Control. 2008 (Year: 2008).*
Steris, Technical Data Monograph: V-PRO® 1 Low Temperature Sterilization System and V-PRO 1® Plus Low Temperature Sterilization System 4-6 (Mentor, Ohio, 2013).
Oerlikon Leybold Vacuum, Fundamentals of Vacuum Technology 67-69 (Cologne, Jun. 2007).

* cited by examiner

APPARATUS AND METHOD FOR DETECTING MOISTURE IN A VACUUM CHAMBER

FIELD

The subject matter disclosed herein relates to the detection of moisture in a chamber in which a vacuum is being drawn. It is particularly useful in chemical vapor sterilization techniques.

BACKGROUND

Medical devices may be sterilized before use in order to minimize the likelihood that a device contaminated by, e.g., microorganisms might be used on a subject, which could cause an infection in the subject. Various sterilization techniques may be employed, using sterilants including one or a combination of steam, ethylene oxide, chlorine dioxide, ozone and hydrogen peroxide. Often the chemical sterilants are employed in a gaseous and/or a plasma form. For these techniques, sterilization is typically conducted within a sterilization chamber of a sterilization system. For certain chemical sterilization techniques, such as those using hydrogen peroxide, the sterilization chamber typically includes a vacuum chamber that is not only capable of achieving low pressures therein, but of also introducing sterilants therein and withdrawing sterilants therefrom. Some chemical sterilization processes, such as those that use ethylene oxide, require water vapor within the vacuum chamber to be effective. However, for other chemical sterilization processes, such as those that use hydrogen peroxide, water in vapor, liquid, or solid form within the vacuum chamber may decrease effectiveness.

A typical chemical vapor sterilization process for medical devices begins with medical-facility personnel preparing the devices for sterilization by washing the instruments with water and/or a washing solution to remove solids and liquids from the instrument. The personnel then dries the instruments, (e.g., using heat, medical-grade compressed air, and/or towels) and perhaps wraps them in a wrap suitable for sterilization, which acts as a barrier to microorganisms but that permits passage of a sterilant therethrough. Instruments wrapped in a wrap are sometimes referred to as a sterilization pack or load. The load is then placed into the vacuum chamber of the sterilization system and the chamber is closed (sealed), typically by closing the chamber's door. The chamber may be heated, which may help vaporize water that may be within the chamber. Next, the atmosphere in the chamber, which may include water vapor, is evacuated. In some sterilization procedures, air within the vacuum chamber may be excited to form an air plasma, which may further aid in vaporizing water for removal from the chamber. After achieving a low pressure, sometimes referred to as a vacuum or a rough vacuum, a sterilant is introduced into the chamber, either in gaseous form or as a mist that vaporizes in the low pressure environment of the chamber. The added gas in the chamber slightly raises the pressure in the chamber. The sterilant spreads quickly throughout the chamber, entering small or confined spaces, such as cracks, crevices, and lumens in the medical devices contained therein. The sterilant bathes the medical devices, which kills bacteria, viruses, and spores disposed upon and within the devices that it contacts. In some sterilization procedures, particularly low-temperature procedures that utilize hydrogen peroxide, the hydrogen peroxide gas may be excited via an electric field to change the gas into a plasma. Finally, the sterilant is evacuated from the chamber and the chamber is returned to the ambient pressure. After the sterilization process has ended, the instruments may be removed from the chamber.

Typically, healthcare personnel check whether the sterilization process was efficacious using various techniques known in the art, e.g., by use of a self-contained biological sterilization indicator, such as the STERRAD® CYCLESURE® 24 Biological Indicator, manufactured by Advanced Sterilization Products, Division of Ethicon US, LLC, located in Irvine, Calif. Confirmation using this biological indicator typically requires about twenty-four hours. During this time, while the effectiveness of the sterilization remains unconfirmed, medical personnel may decide not use the medical devices. This may cause inventory management inefficiencies for a health care provider, such as a hospital, because, for example, the medical devices should be stored while they cannot be used, perhaps requiring the health care provider to keep more medical devices in its inventory than it otherwise would to ensure a sufficient supply of medical devices. Alternatively, health care providers may use the medical devices before the sterilization confirmation is completed and sterilization efficacy confirmed. However, using the medical devices before sterilization efficacy has been confirmed may expose a subject of a medical procedure to risk of infection from the medical devices. Given the total amount of time medical devices may be unsuitable for use because of the time required to conduct a sterilization process and the time required to confirm that the sterilization process was efficacious, healthcare personnel desire updated sterilization processes and confirmation techniques that require less time to conduct and reduce the likelihood that a process may fail as compared to those presently available.

An example of a commercially available sterilization chamber is the STERRAD® 100NX® System manufactured by Advanced Sterilization Products, Division of Ethicon US, LLC, located in Irvine, Calif. The 100NX® is advertised as being capable of sterilizing most general surgical instruments in 47 minutes. The cycle temperature of the 100NX® is advertised as being between 47° C. to 56° C. These temperatures are preferred for helping to vaporize residual water with heat without over-heating the instrument, which could compromise the function or structure of instruments. Further, these temperatures are preferred for generating plasma, which helps improve the effectiveness of the sterilization process and further helps vaporize any residual water, and to aid in removing hydrogen peroxide from the vacuum chamber.

Commercially available sterilization systems that employ, e.g., hydrogen peroxide are designed to preferably operate without any water in their sterilization chambers. If healthcare personnel erroneously introduced water into the chamber, the water will begin evaporating as the pressure within the chamber is lowered to maintain a surface-pressure equilibrium between the water and its surroundings. This pressure equilibrium, which is also a function of temperature, is typically referred to as the vapor pressure of water. At 100° C., the vapor pressure of water is one atmosphere, or 760 torr, which is why it is commonly stated that water boils at 100° C. However, when the local pressure around water is less than 760 torr, the liquid water may change phase to water vapor at lower temperatures.

Latent heat is required for water to change phase to vapor. The evaporating water may draw at least some of this energy from remaining water, which lowers the temperature of the remaining water. As the pressure in the chamber continues to drop, and as evaporating water continues to lower the temperature of the remaining water, the pressure and temperature approach what is often referred to as the "triple-point" of water, i.e., the temperature and pressure combination at which ice, water, and water vapor exist in equilibrium. The triple-point temperature of water is 0.01° C. and the triple-point pressure of water is 4.58 torr. As the temperature and pressure approach the triple-point, the likelihood of ice-crystals forming within the remaining water increases.

Ice may inhibit contact of a sterilant with at least a portion of a medical device or instrument, including by potentially blocking lumens of the device. Accordingly, ice may cause a sterilization process to be inefficacious, which may lead to use of a non-sterile device on a subject or cause a hospital to subject the device to another round of sterilization, which requires additional valuable time. Moreover, sterilant may condense upon or become trapped within the ice, which could lead to chemical burns on the skin of medical personnel.

In addition to sterility itself, time and efficiency associated with sterilization processes for medical devices are important considerations for health care facilities. For example, hospitals often prefer to maximize the number of times a device may be used within a given time span, e.g., per week. Subjecting a wet medical device to a sterilization process thus not only increases the likelihood that the sterilization process will not be efficacious, it also wastes time and may lower the number of times per week that a device may be reused. Accordingly, medical personnel should remove all water from the medical devices after they have been cleaned but before they are placed into the sterilization chamber, or at least before sterilant gas is introduced into the vacuum chamber.

Some sterilization systems check for the presence of water in the sterilization chamber before they introduce a sterilant gas therein by checking for small increases in pressure inside the chamber while vacuum is being drawn. If no water is present in the chamber while vacuum is being drawn, the pressure decreases asymptotically without any increases therein. However, if any water is in the chamber while vacuum is being drawn, at least some of the water may turn to vapor, which may cause slight local increases in pressure. Accordingly, detection of a small pressure increase while vacuum is being drawn indicates the presence of water in the vacuum chamber. When water is detected, the sterilization process may be aborted so that excess water may be removed from the medical devices before attempting sterilization again. Aborting a sterilization process as soon as water is detected may help save time and resources as compared to continuing a sterilization process that may not be efficacious, and may help avoid use of a non-sterile device.

In some instances, instead of aborting the sterilization process, it may be preferable to attempt to remove the water from the vacuum chamber by a process called "load conditioning." Load conditioning is typically accomplished by, first, some combination of heating and/or introducing plasma into the sterilization chamber and re-pressurizing the sterilization chamber to transfer energy to the water (or ice), and, second, drawing a vacuum anew to convert the water to vapor. Load conditioning may occur before, after, or both before and after vacuum is drawn in the chamber. In some instances load conditioning cannot remove water from the chamber. In other instances load conditioning may remove some but not all of the water. In such instances, additional load conditioning may be attempted, but doing so requires additional time and resources. Accordingly, where load conditioning cannot remove water from the chamber or where repeated attempts may be required to remove water, it may be desirable to forego load conditioning in favor of aborting the process so that excess water may be removed from the medical devices before attempting a new sterilization process.

SUMMARY

The disclosed subject matter concerns methods of operating a sterilization system having a vacuum chamber for sterilizing instruments. The chamber is connected to a reservoir of sterilant by a valve in a closed state. A first example method may include placing the instruments in a non-sterile state in a sterilization pack, opening the chamber, placing the pack into the chamber; placing a biological indicator into the chamber, closing the chamber, withdrawing a first volume of air from the chamber, changing a volume of liquid water into vapor, opening the valve, introducing the sterilant into the chamber, withdrawing the sterilant from the chamber, introducing a second volume of air into the chamber, opening the chamber, removing the pack from the chamber, and removing the instruments in a sterile-state from the pack. The first example method may further include the steps of repeatedly determining pressure within the chamber while withdrawing air from the chamber, calculating a first second-derivative value of pressure with respect to time corresponding to a pressure greater than approximately the triple-point pressure of water, calculating a second second-derivative value of pressure with respect to time corresponding to a pressure greater than approximately the triple-point pressure of water and a time subsequent to the time corresponding to the first second-derivative value, calculating a third second-derivative value of pressure with respect to time corresponding to a pressure less than approximately the triple-point pressure of water and a time subsequent to the time corresponding to the second second-derivative value, calculating a fourth second-derivative value of pressure with respect to time corresponding to a pressure less than approximately the triple-point pressure of water and a time subsequent to the time corresponding to the third second-derivative value, determining that the fourth second-derivative value is less than or equal to the third second-derivative value, and determining that the second second-derivative value is less than or equal to the first second-derivative value.

A second example method of operating a sterilization system having a vacuum chamber may include the steps of initiating a timer in a digital computer, withdrawing a first volume of air from the chamber, repeatedly determining pressure within the chamber while withdrawing the first volume of air from the chamber, calculating, with the digital computer, a first second-derivative value of pressure with respect to time, calculating, with the digital computer, a second second-derivative value of pressure with respect to time, the second second-derivative value corresponding to a time subsequent to the time corresponding to the first second-derivative value, determining, with the digital computer, that the second second-derivative value is greater than the first second-derivative value, and automatically introducing a second volume of air into the chamber. In the second example method, the step of repeatedly determining the pressure may further include the steps of repeatedly taking pressure measurement data and storing the data in a non-transitory storage medium of the digital computer. This example method may also include determining, with the digital computer, that the second second-derivative value occurs at a pressure less than approximately the triple-point pressure of water. In the second example method, the step of automatically introducing air into the chamber may further include the step of automatically opening a valve, automatically opening the chamber, and closing the chamber. The second example method may also include the step of initiating the timer after the step of closing of the chamber. The second example method may also include the step of withdrawing a first volume of air from the chamber after the step of initiating the timer. In some versions of the second example method, no sterilant may be introduced into the vacuum chamber. The second example method may also include the step of determining that the difference between the second second-derivative value and the first second-derivative value is greater than a noise floor.

A third example method of operating a sterilization system having a vacuum chamber for sterilizing instruments may include the steps of initiating a timer in a digital computer, withdrawing a first volume of air from the chamber, repeatedly determining pressure within the chamber while withdrawing the first volume of air from the chamber, calculating, with the digital computer, a first second-derivative value of pressure with respect to time, calculating, with the digital computer, a second second-derivative value of pressure with respect to time, the second second-derivative value corresponding to a time subsequent to the time corresponding to the first second-derivative value, determining, with the digital computer, that the second second-derivative value is greater than the first second-derivative value, and automatically introducing energy into the chamber. In the third example method, the step of repeatedly determining the pressure may include repeatedly taking pressure measurement data and storing the data in a non-transitory storage medium of the digital computer. The third example method may also include determining, with the digital computer, that the second second-derivative value occurs at a pressure greater than approximately the triple-point pressure of water. In the third example method, the step of introducing energy to the chamber may include at least one of automatically heating the chamber, automatically opening a valve to introduce air into the chamber that is warmer than the chamber, and automatically generating a plasma. The third example method may also include the step of closing the chamber, wherein the step of initiating the timer occurs after the step of closing of the chamber. In the third example the step of withdrawing the first volume of air from the chamber may begin after the step of initiating the timer.

A fourth example method of operating a sterilization system having vacuum chamber for sterilizing instruments may include the steps of initiating a timer in a digital computer, withdrawing a first volume of air from the chamber, repeatedly determining pressure within the chamber while withdrawing the first volume of air from the chamber, calculating, with the digital computer, a first second-derivative value of pressure with respect to time, calculating, with the digital computer, a second second-derivative value of pressure with respect to time, the second second-derivative value corresponding to a time subsequent to the time corresponding to the first second-derivative value, determining, with the digital computer, that the second second-derivative value is less than the first second-derivative value, and automatically introducing a sterilant gas into the chamber. In the fourth example method, the step of repeatedly determining the pressure includes repeatedly taking pressure measurement data and providing the data to a non-transitory storage medium of the digital computer. The fourth example method may also include the step of maintaining a sterilization-appropriate pressure within the chamber. The sterilization-appropriate pressure is maintained for at least one second. The sterilization-appropriate pressure may be between approximately 4 torr and approximately 0.1 torr. The sterilization-appropriate pressure may be approximately 0.3 torr. In the fourth example method, the step of automatically introducing the sterilant gas into the chamber may occur after the step of maintaining the sterilization-appropriate pressure for at least one second. In the fourth example method, the step of automatically introducing the sterilant gas into the chamber may include opening a valve. The fourth example method may also include the step of placing the instruments in a non-sterile state into the chamber and closing the chamber before the step of withdrawing the first volume of air from the chamber. The further example method may also include the step of opening the chamber and removing the instruments in a sterile-state from the chamber.

A fifth example method of operating a sterilization system having a vacuum chamber for sterilizing instruments may include the steps of initiating a timer in a digital computer, withdrawing a first volume of air from the chamber, repeatedly determining pressure within the chamber while withdrawing the first volume of air from the chamber, calculating, with the digital computer, second-derivative values of pressure with respect to time, calculating, with the digital computer, a summation of positive differences between consecutive second derivative values, comparing the summation to a threshold value, opening a valve, and opening the chamber. In the fifth example method the summation may be greater than the threshold value and the step of opening the valve may cause the pressure in the chamber to increase. In the fifth example method, the pressure in the chamber may be increased by a second volume of air flowing past the valve and into the chamber. The fifth example method may also include the step of vaporizing a volume of water. In the fifth example method, the summation may be less than the threshold value and the step of opening the value may allow a sterilant to be introduced into the chamber. In the fifth example method, the summation may be a first summation that is terminated when a difference between consecutive second derivative values is negative. In the fifth example method, a second summation may be commenced when a difference between consecutive second derivative values is positive.

As used herein, the term "noise floor" concerns a plot of pressure data versus time wherein the pressure data was output from a pressure transducer connected to a vacuum chamber. The term noise floor refers to the peak to peak amplitude between the greatest local maximum on the plot caused by noise inherent in the pressure transducer and the least local minimum on the plot caused by noise inherent in the pressure transducer when the vacuum chamber is maintained at or near the lowest pressure the vacuum chamber may maintain or at or near a desired final pressure for a given sterilization process. The noise floor may be determined empirically for a given vacuum chamber or a given sterilization process.

BRIEF DESCRIPTION OF THE DRAWINGS

While the specification concludes with claims that particularly point out and distinctly claim the subject matter described herein, it is believed the subject matter will be better understood from the following description of certain examples taken in conjunction with the accompanying drawings, in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

I. A Sterilization System

Figure 1:
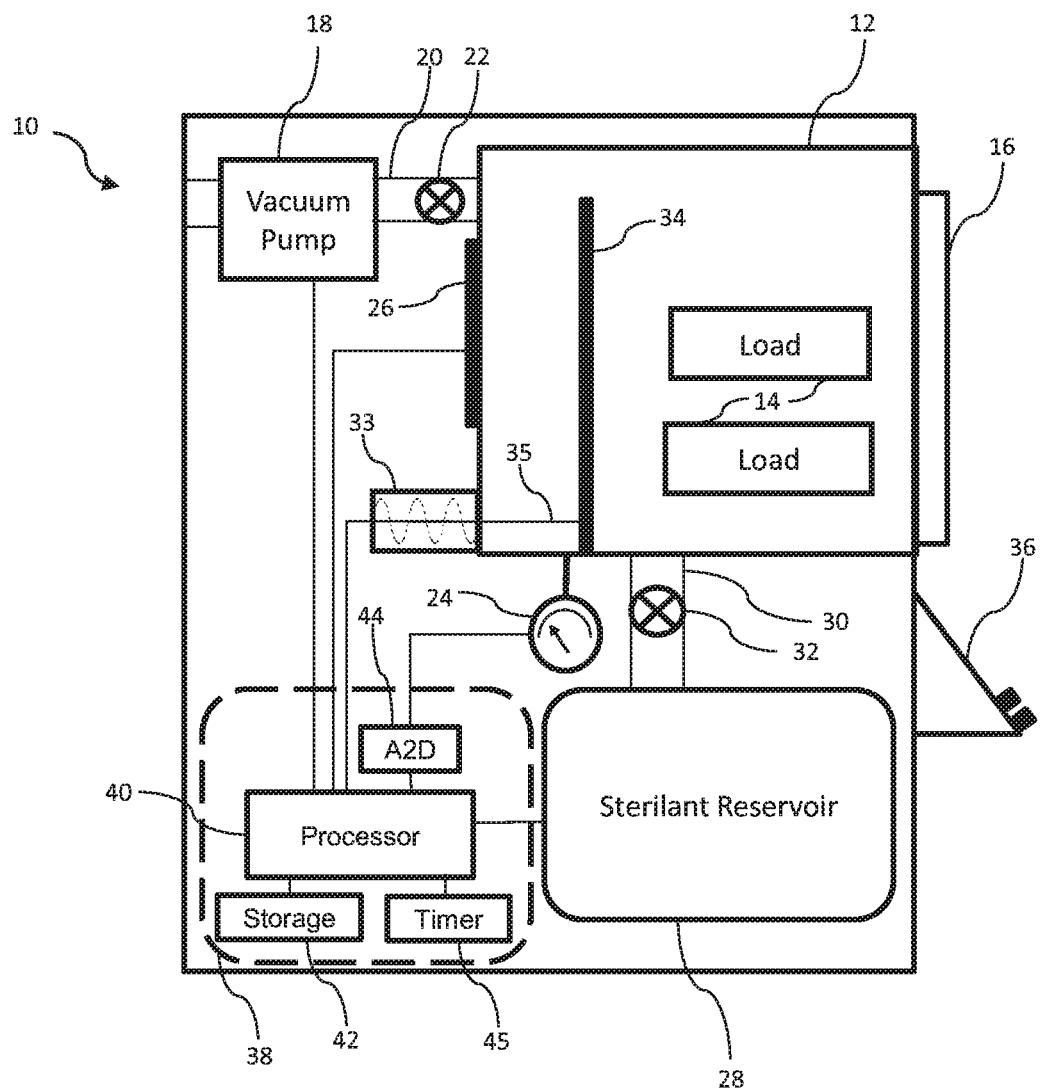
FIG. 1 depicts, in block diagram form, a sterilization system having a vacuum chamber that may be used to practice the methods disclosed herein.

FIG. 1 reflects a sterilization system 10, depicted schematically in block diagram-format. It comprises, a vacuum chamber 12 having a load (pack) 14 of instruments therein to be sterilized. The chamber 12 may be formed of any material that is sufficiently robust to handle pressures as low as approximately between 0.3 torr and 3 torr, and sufficiently inert to avoid reacting with or absorbing any sterilants introduced therein. Such materials may include aluminum and stainless steel. Chamber 12 may also include an openable and sealable barrier 16, such as a door, that may be opened to allow placement and removal of load 14 into chamber 12. The barrier should be sufficiently robust, and include a sufficiently robust seal, to withstand low pressures drawn within chamber 12 and avoid leaks between chamber 12 and the ambient environment. A vacuum pump 18 capable of reaching the desired operating pressure evacuates air and other gases, such as water vapor, from chamber 12. Vacuum pump 18 may include a hose or pipe 20 to connect it to chamber 12. Vacuum pump 18 may also include a valve 22, which may be open or closed to assist or prevent pressure changes in chamber 12. For example, when the valve is open and the vacuum pump is operational, the pressure in chamber 12 may be lowered. Alternatively, when the valve is open and the vacuum pump is not operational, the pressure in the chamber may be equalized to the ambient pressure. In other embodiments, a valve that is not part of vacuum pump 18 may be used to control whether chamber 12 has a pressure equal to the ambient pressure. A pressure monitor 24 monitors the pressure in chamber 12. Particularly suitable pressure monitors are capacitance manometers available from MKS Instruments. A heating element 26 may be used to heat the chamber 12. It may comprise separate elements bonded to the outside of the chamber 12 in locations sufficient to uniformly heat the chamber 12. A tank or reservoir 28 containing sterilant, which includes a hose or pipe 30, is connected to chamber 12. In some embodiments, tank 28 may further include a valve 32, which may be disposed between chamber 12 and tank 28 to control the flow of sterilant from tank 28 through hose 30 and into chamber 12. A power source and/or signal generator 33 and an electrode 34 disposed within chamber 12 may be provided to create an electric field within chamber 12 between electrode 34 and the interior surface of chamber 12 to create a plasma therein. A signal, such as an RF signal, may be provided to electrode 34 from generator 33 by way of a feed through 35, such as a wire-type feed through. Creation of a plasma is useful for low temperature sterilization processes that use hydrogen peroxide gas. In these processes, the hydrogen peroxide gas may be excited to form a hydrogen peroxide plasma. Alternatively, another gas may be used to form the plasma, such as air, which may help lower hydrogen peroxide residuals upon the load to facilitate removal of hydrogen peroxide from chamber 12. Sterilization system 10 may also include a user interface 36, that may include output devices, such as a printer or display, and user-input devices, such as a keypad or touch screen.

A control system 38, such as a digital computer, controls the operation of the system 10 and its various components. Control system 38 may employ one or more microprocessors 40. It may also employ a non-transitory storage medium 42, such as random access memory (RAM), a hard-disk drive, or flash memory, which can store data, such as pressure values and time values. An analog to digital (A2D) converter 44 may be used to convert analog data to digital data if analog data, such as pressure data, is collected. A timer or clock circuit 45 keeps time. Control system 38 may further include software and/or logic by which the microprocessor may numerically compute values for first derivatives of pressure with respect to time and values for second derivatives of pressure with respect to time. Such numerical calculations may be performed according to the forward difference, backwards difference, central difference, or some combination thereof, as is known in the art. These first-derivative values and second-derivative values may also be stored in storage medium 42. Control system 38 may further include software and/or logic by which the microprocessor may compare first-derivative values corresponding to different pressures and different times. Control system 38 may further include software and/or logic by which the microprocessor may compare second-derivative values corresponding to different pressures and different times. For example, the control system is capable of storing pressure values $P_i$, which are measured at various time increments i. The amount of time between neighboring time increments, designated $\Delta t$, may be equal to approximately 0.1 second, approximately 1 second, approximately 2 seconds, approximately 5 seconds, or approximately 10 seconds. The pressure values may also be expressed as a function of time such that $P_i$ may be expressed as $P(t_n)$ where $t_n = t_{n-1} + \Delta t$. The pressure values may be measured throughout the sterilization process and stored in storage medium 42. The pressure values may also be measured and stored at least while the system is drawing a vacuum in the vacuum chamber. The pressure values may also be measured and stored at least while the pressure in the vacuum chamber is below approximately 30 torr.

II. Detecting Residual Water

First-derivative values of pressure with respect to time $(dP(t_n)/dt)$ and second-derivative values of pressure with respect to time $(d^2 P(t_n)/dt^2)$ may be computed for all or mostly all pressure values, $P_i$ or $P(t_n)$, by the microprocessor and stored in storage medium 42. The first and second derivatives may be calculated numerically, as is known in the art. The first and second derivatives may be calculated on a running basis, e.g., while vacuum is being drawn, or after a predetermined pressure is achieved in the chamber. Due to the nature of numerical calculations of first derivatives and second derivatives, there may be a time lag between the pressure, its first derivative with respect to time, and its second derivative with respect to time. In other words, for example, a local maximum in a plot of the second derivative of pressure versus time may be observed approximately one tenth of a second, approximately one half of a second, approximately one second, approximately two seconds, approximately five seconds, or some other time after the pressure to which it corresponds. The amount of time of the delay is a function of the technique used to calculate the derivative.

In a typical sterilization process where there is no water or other potential sources of gas (excluding air) within the vacuum chamber at the beginning of the process, the pressure in the vacuum chamber during the vacuum draw may be described theoretically by the equation $$\mathrm{Log}_e[P] = -\frac{S*t}{V}$$

for pressures between approximately atmospheric pressure and approximately 750 mTorr, where P is pressure, S is vacuum-pump speed, t is time, and V is volume of the vacuum chamber.

Figure 2:
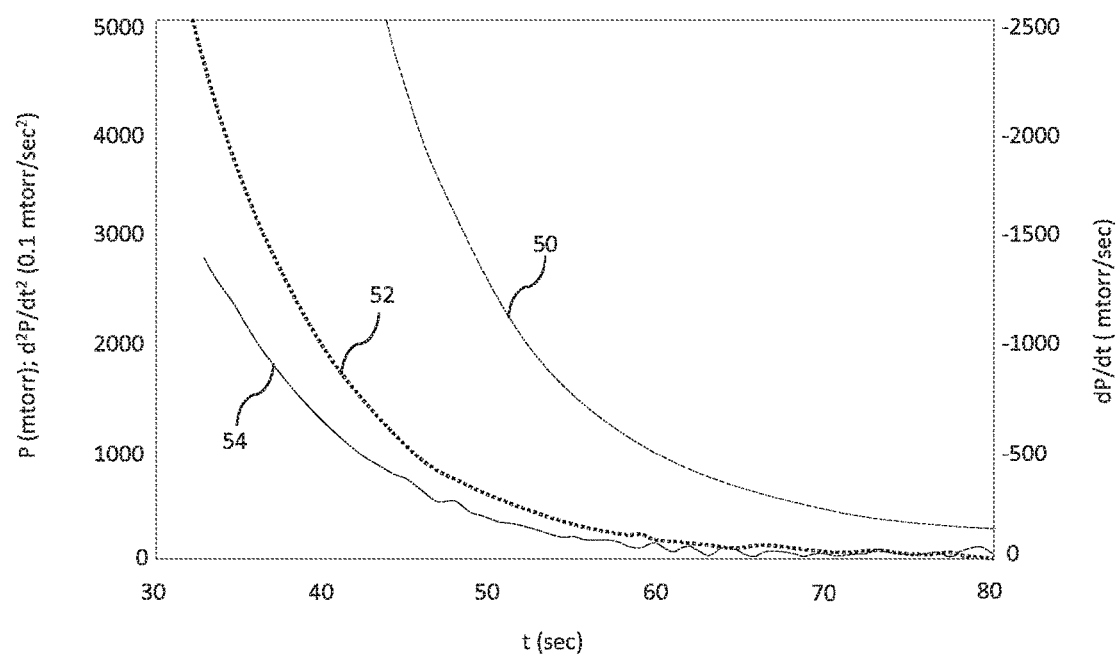
FIG. 2 is a graph plotting pressure versus time, a first derivative of pressure versus time, and a second derivative of pressure versus time, in the vacuum chamber depicted in FIG. 1, when no water is in the chamber.

FIG. 2 reflects a graph upon which are plotted approximate pressure versus time data 50 for pressures under 5000 millitorr between 30 seconds and 80 seconds into a vacuum draw during a sterilization process in which no residual water (or other sources of gas) was within the vacuum chamber. Also included on this graph are first derivative of pressure values 52, which may be calculated from pressure versus time data 50, and second derivative of pressure values 54, which may be calculated from pressure versus time data 50 and first derivative versus time values 52. Pressure data 50 are the dashed line, first derivative values 52 are the dotted line, and second derivative values 54 are the solid line. Pressure data 50 decreases asymptotically until a desired minimum pressure of the sterilization process is achieved. The first derivative values 52, reflected in units of millitorr per second, and second derivative values 54, reflected in units of 0.1 millitorr/second squared, also decrease asymptotically. Although noise in the pressure data 50 is not apparent in this graph, and noise in the first derivative values 52 is minimally apparent, a noise floor is apparent in the second derivative values 54. There is a noise floor of about 6 millitorr per second squared for second derivative values 54.

In some instances, particularly where the instruments to be sterilized are not sufficiently dried by healthcare personnel, residual water may be introduced into the vacuum chamber. In these instances, water may be in the vacuum chamber when the vacuum draw of the sterilization process commences. As the pressure in the chamber decreases, at least a partial volume of the residual water may change phase to gas. At pressures equal or less than to approximately 4.58 torr (the triple point pressure of water), the phase change to gas may be further caused by a corresponding phase change to ice. That is, as ice crystals within the residual water form, latent heat is released, which heats neighboring portions of water. Because the three phases of water—gas, liquid, and solid—exist in equilibrium at the triple-point and in near-equilibrium at pressures and temperatures close to the triple point, the latent heat from the phase change to ice of some residual-water molecules may supply energy to other residual-water molecules that causes them to change phase to gas. When liquid water changes phase to gas, irrespective of whether ice is also formed, a new volume of gas is suddenly present in the vacuum chamber, which may cause an increase in the rate of pressure change, which may even be sufficient to cause a local increase in pressure.

Figure 3:
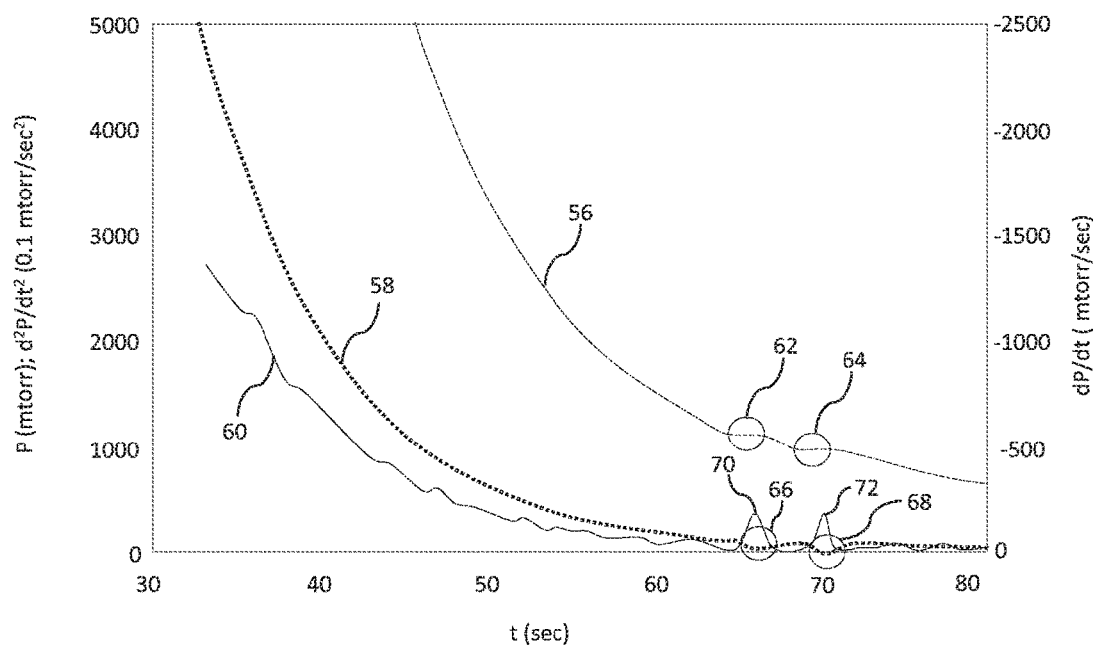
FIG. 3 is a graph plotting pressure versus time, a first derivative of pressure versus time, and a second derivative of pressure versus time, in the vacuum chamber depicted in FIG. 1, when water is in the chamber on a non-metallic surface.

FIG. 3 reflects a graph upon which are plotted approximate pressure versus time data 56 for pressures under 5000 millitorr between 30 seconds and 80 seconds into a vacuum draw. Pressure data 56, reflected in units of millitorr, corresponds to a vacuum draw during which approximately 0.1 milliliters of residual water was within the vacuum chamber, disposed upon a plastic sterilization rack. FIG. 3 also reflects first derivative of pressure values 58, which may be calculated from pressure versus time data 56, and second derivative of pressure values 60, which may be calculated from pressure versus time data 56 and first derivative versus time values 58. Pressure data 56 are the dashed line, first derivative values 58 are the dotted line, and second derivative values 60 are the solid line. The first derivative values 58 are reflected in units of millitorr per second and second derivative values 60 are reflected in units of 0.1 millitorr/second squared. As shown in FIG. 3, between approximately t=65 seconds and approximately t=70 seconds, at pressures equaling approximately 1200 millitorr and approximately 1000 millitorr, the curvature of the pressure data 56 changes as indicated by circles 62 and 64, which corresponds to a decrease in the rate of pressure change, such that, momentarily, there is little if any decrease in the pressure. The data suggest that the rate of change of pressure within the vacuum chamber decreased when water changed phase to gas. These changes are reflected in local minima of the plotted first-derivative values as indicated by circles 66 and 68. Related changes in the curvature of the plotted second-derivative values are indicated by local maxima 70 and 72. Local maxima 70 and 72 are more readily apparent and easier to detect than the changes in curvature to the pressure data and first-derivative values indicated by circles 62, 64, 66, and 68. Accordingly, the second-derivative of pressure with respect to time may assist a determination of whether moisture may be in the chamber during the vacuum draw.

Figure 4:
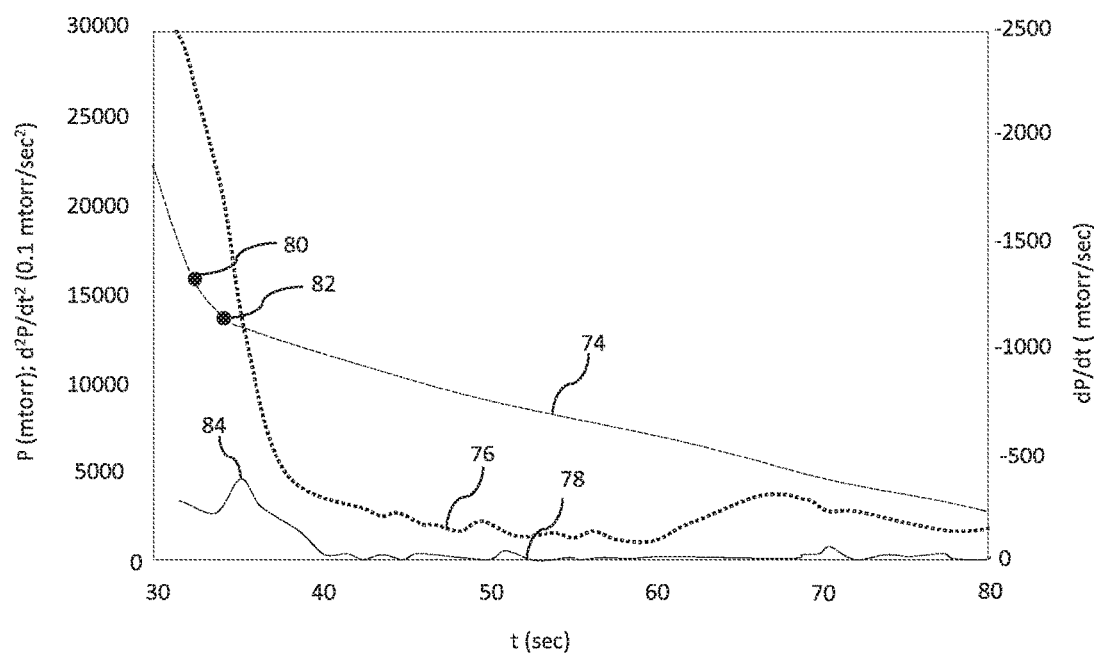
FIG. 4 is a graph plotting pressure versus time, a first derivative of pressure versus time, and a second derivative of pressure versus time, in the vacuum chamber depicted in FIG. 1, when water is in the chamber on a metallic surface.

FIG. 4 reflects a graph upon which are plotted approximate values of pressure versus time data 74 for pressures less than 30000 millitorr between 30 seconds and 80 seconds into a vacuum draw. Pressure data 74, reflected in units of millitorr, correspond to a vacuum draw during which approximately 1.5 milliliters of residual water was within the vacuum chamber, disposed upon an aluminum sterilization rack. FIG. 4 also reflects first derivative of pressure values 76, which may be calculated from pressure versus time data 74, and second derivative of pressure values 78, which may be calculated from pressure versus time data 74 and first derivative versus time values 76. Pressure data 74 are the dashed line, first derivative values 76 are the dotted line, and second derivative values 78 are the solid line. The first derivative values 76 are reflected in units of millitorr per second, and second derivative values 78 are reflected in units of 0.1 millitorr/second squared. As shown in FIG. 4, at approximately t=32 seconds and a pressure of approximately 15,000 millitorr, indicated by reference numeral 80, the curvature of pressure data 74 begins to change, indicating that the rate of pressure change is decreasing. The largest degree of curvature change appears at approximately t=33 seconds and a pressure of approximately 14000 millitorr, as indicated by reference numeral 82. The data suggest that the rate of change of pressure within the vacuum chamber decreased when water changed phase to gas. Local maximum 84 of the plot of the second derivative values 78 corresponds to the time and pressure at which the change in the rate of the pressure change was greatest. Further local maximum 84 is more readily apparent and easier to detect than the changes in curvature to the pressure data and first-derivative values. Accordingly, the second-derivative of pressure with respect to time may assist a determination of whether moisture may be in the chamber during the vacuum draw.

Sterilization processes, including those that may include load conditioning, (i.e., a process for removing residual water from a load in a vacuum chamber) sometimes cancel when residual water is in the vacuum chamber. Some commercially available sterilizers are designed to attempt to determine when there is too much water vapor, or another gas, in the chamber for sterilization to be effective and/or for the system's load conditioning cycle to be effective, such that it would simply be more efficient for healthcare personnel to remove the load from the system and try to dry it again. For example, some systems check for increases in pressure under conditions where pressure should remain constant, while others simply abort the sterilization cycle if the vacuum draw requires more time than it should. However, these checks may be insufficient for smaller amounts of water, which the technology described herein addresses. Moreover, the inventors have determined that the likelihood of sterilization and/or load-conditioning success depends on whether the water is disposed on metallic or a non-metallic surface because metallic surfaces may conduct heat to the water whereas non-metallic surfaces do not, increasing the likelihood of ice formation. Accordingly, the likelihood of avoiding sterilization and/or load-conditioning failure may be increased by determining whether the residual water is disposed on metallic or non-metallic surfaces, and, correspondingly, whether ice may form during vacuum draw. Because load conditioning may not be suitable for efficiently removing ice once it has formed, in some sterilization processes, it may be desirable to perform a load-conditioning operation before vacuum is drawn. This may be performed by heating the vacuum chamber with the aim of vaporizing at least some of the water that may be disposed within the chamber. In some embodiments, the chamber may be heated at pressures below atmospheric pressure.

Using techniques described herein, detectable phase changes of liquid water to water vapor during vacuum draw may occur at vacuum-chamber temperatures less than approximately 60° C. and above the triple-point pressure of water, e.g., between approximately 5 torr and approximately 30 torr, when residual water in the chamber is disposed upon a metallic surface. Because metallic objects typically have a high thermal conductivity, particularly as compared to non-metallic objects, metallic objects are able to transfer energy to water disposed upon its surfaces, which raises the temperature of the water and enables phase changes of water from liquid to gas. Phase changes of liquid water to water vapor during vacuum draw are less likely in this temperature and pressure regime when liquid water is disposed upon non-metallic surfaces. Non-metallic objects generally do not transfer sufficient energy to the liquid water to enable it to change phase to gas.

Detectable phase changes of liquid water to water vapor during vacuum draw may also occur at vacuum-chamber temperatures below approximately 60° C. and below approximately the triple-point pressure of water (4.58 torr) when residual water in the chamber is disposed upon a nonmetallic surface. As the pressure drops toward and past the triple-point pressure, the water may change phase to water vapor and the temperature of residual water may correspondingly drop, which may cause ice crystals to form in the residual water. When ice is formed, latent heat is released. Because the water is at or near the triple point, this latent heat may be sufficient to enable neighboring water molecules to change phase to gas as the pressure continues to drop.

Based on the foregoing, phase changes that occur at pressures above the triple-point pressure of water indicate that at least some residual water was disposed on a metallic surface and that the phase change to vapor may not include a corresponding phase change to ice. However, phase changes that occur at pressures near or below the triple-point pressure of water indicate that at least some residual water may have been disposed on a non-metallic surface and that the phase change to vapor may include a corresponding phase change to ice. Accordingly, when a local maximum to the curve of the second derivative of pressure with respect to time occurs at a pressure greater than the triple-point pressure, it is likely that water is disposed upon a metallic surface, indicating that ice formation did not accompany the vaporization. However, when a local maximum to the curve of the second derivative of pressure with respect to time occurs at or below the triple-point pressure, it is likely that water is disposed upon a non-metallic surface, indicating that ice formation accompanied the vaporization.

The inventors believe that they were the first to discover and disclose what is described in the preceding paragraph. They have determined a new, useful, and inventive application thereof, described below, which improves sterilization processes and load-conditioning techniques known in the art. This application involves assessing whether it is advisable to perform a load-conditioning process, whether a load should be manually re-dried, and whether a load is sufficiently dry to be introduced to a sterilant.. This assessment may be accomplished by determining the pressure at which a local maximum of the second-derivative of pressure with respect to time occurs. If at least one local maximum occurs beneath the triple-point pressure of water, it may be preferable to abort the sterilization process instead of attempting load-conditioning because of the possibility that ice crystals may have formed within the water and upon the load. However, if local maxima are detected above the triple-point pressure of water and no local maximum is detected beneath the triple-point pressure of water, load-conditioning may be attempted because the water that may remain upon the load may be readily vaporized and evacuated from the vacuum chamber without creating ice crystals upon the load.

Because of measurement error associated with the pressure values, such as errors caused by resolution of a pressure transducer and analog-to-digital conversions, noise may be present in the data, calculations, and curves of pressure vs. time, first derivative of pressure vs. time, and second derivative of pressure vs. time. In order to avoid mistakenly determining that a local maximum in the second derivative curve exists that does not correspond to an increase in pressure but that is caused by measurement error, the value of the local maximum should be sufficiently greater than the noise floor.

It may be preferable to base a determination of whether to condition a load or abort a cycle on the relative size of a local maximum as compared to e.g., an inflection point, a local minimum, or the noise floor. Alternatively, it may be preferable to base this decision on a summation of positive differences between consecutive second derivative values, which is referred to as $\delta_+$. $\delta_+$ may be calculated according to the following steps. After or during the vacuum draw, the second derivative of pressure with respect to time may be calculated and stored for each time increment. Differences between neighboring, i.e., consecutive, second derivative values may be calculated by subtracting the second derivative value calculated for one time increment from the second derivative value calculated for the following time increment. If the value of this difference is positive, (i.e., if the value of the second derivative increased), the value of the difference is summed. If the value of this difference is negative (i.e., if the value of the second derivative decreased), the value of the difference is disregarded. This summation procedure for $\delta_+$. may be expressed by the following formula:

$$\delta_+ = \sum_{n=1}^{m} \left( \frac{d^2 P(t_n)}{dt^2} - \frac{d^2 P(t_{n-1})}{dt^2} \right) \text{ if } \frac{d^2 P(t_n)}{dt^2} > \frac{d^2 P(t_{n-1})}{dt^2}.$$

In the foregoing formula, m corresponds to the number of time increments within the given or chosen time period over which $\delta_+$ is calculated. Also, in the foregoing formula, $t_n = t_{n-1} + \Delta t$. As noted above $\Delta t$ is the duration of a time between time increments, and may be equal to approximately 0.1 second, approximately 1 second, approximately 2 seconds, approximately 5 seconds, or approximately 10 seconds. When $\delta_+$ is calculated in this fashion, a single $\delta_+$ may be calculated for a desired range of pressures. For example, a single $\delta_+$ may be calculated for the pressure range of, e.g., between approximately the triple-point pressure of water (i.e., approximately 4.6 torr) and the lowest pressure achieved in a vacuum chamber during a sterilization process (e.g., approximately 0.3 torr). $\delta_+$ may be calculated for any other range of pressures that a healthcare facility or a sterilization system manufacturer may prefer. For example, it may be desired to calculate multiple $\delta_+$ for subranges of pressures within a larger pressure range.

Alternatively, the calculation of $\delta_+$ according to the summation formula set forth above may be limited to only consecutive increases in the value of the differences between consecutive second derivatives of pressure with respect to time that are not separated by any decreases in the value of these differences. For example, assume that five consecutive values for $d^2P(t_n)/dt^2$ are calculated respectively to have magnitudes of 10, 9, 11, 12, and 9—each having units of mtorr/s$^2$. The changes from 10 to 9 and 12 to 9 are disregarded because the differences between the neighboring values are negative. The changes from 9 to 11 and 11 to 12 are summed because the differences between the neighboring values are positive. Accordingly, $\delta_+ = (11-9) + (12-11) = 3$ mtorr/s$^2$. When $\delta_+$ is calculated in this fashion, multiple $\delta_+$ may be calculated during a vacuum draw, and each may be individually compared to a threshold. For example, assuming that ten consecutive values for $d^2P(t_n)/dt^2$ are calculated respectively to have magnitudes of 10, 9, 11, 12, 9, 13, 14, 9, 12, and 9, three different $\delta_+$ would be calculated as 3, 5, and 3.

$\delta_+$ may be determined via experiments to correspond with an amount of water that may have been present in a vacuum chamber when the calculation of a $\delta_+$ began. Accordingly, $\delta_+$ may be utilized as a threshold condition from which it may be determined that a load-conditioning routine may be conducted, a sterilization cycle canceled, and/or that the load may be sufficiently dry for sterilization. As noted above, when a phase change of liquid water to vapor occurs and is detected in a vacuum chamber at a pressure less than the triple-point pressure of water (4.58 torr), load-conditioning techniques might be unable to remove water from the chamber, e.g., when there is greater than approximately 5 ml of water in the chamber. However, for smaller quantities of water, e.g., between approximately 1 ml and 5 ml, it may be desirable to attempt to condition a load. Moreover, it is useful to know whether the vacuum chamber is dry, e.g., with less than approximately 1 ml of water contained therein, such that the sterilization system may commence sterilization of the load.

Experiments were performed in order to establish a threshold against which $\delta_+$ may be compared to determine whether moisture may be present in a load. In these experiments, $\delta_+$ was calculated according to the foregoing example, where the calculation is limited to consecutive increases in the value of the second derivative of pressure with respect to time. The data from these experiments suggest that, for pressures less than approximately 4.6 torr, a $\delta_+$ of less than approximately 10 mTorr/s$^2$ indicates that a phase change of liquid water to water vapor did not occur over the time span for which a $\delta_+$ was calculated, whereas a $\delta_+$ of 110 mTorr/s$^2$ or more corresponds to a load that contains too much moisture to be conditioned efficiently and/or sufficiently quickly. Accordingly, for a $\delta_+$ between approximately 10 mTorr/s$^2$ and 110 mTorr/s$^2$, it may be desirable to attempt load conditioning or to abort a sterilization cycle, depending on the preferences and/or requirements of a manufacturer, healthcare facility, and/or healthcare personnel. It should be appreciated, however, by those of skill in the art, that these values for $\delta_+$ are also a function of the sterilization system used, the load contained therein, and environmental factors. The general contours of the experiment that produced the foregoing results for $\delta_+$ are thus set forth herein purely for informational purposes.

The load configuration for this experiment included an instrument tray containing a rack for holding small medical vials in an unsealed Tyvek® pouch. The load was placed into a STERRAD® 100NX® sterilization system. Various experimental runs were conducted where the environmental conditions were varied between 18° C. and 85% relative humidity ("RH"), 25° C. and 50% RH, and 35° C. and 50% RH. Further, these runs were conducted with no water added to the load, 1 ml added to the load, or 5 ml added to the load. Pressures were measured every one second as the pressure dropped from approximately 4.6 Torr to approximately 800 mTorr. From these measured pressures, $\delta_+$ was calculated. Multiple runs were performed at each environmental condition for each amount of water. Values calculated for $\delta_+$, in units of mTorr/s$^2$ are provided in Table 1. Although water was deposited on the test samples as droplets, a threshold based on $\delta+$ may further be used to account for total moisture on or within a load that exists in forms besides drops, such as puddles, tube blockages, or a sheet (e.g., formed by condensation).

TABLE 1

| Amount of water | 18° C., 85% RH | 25° C., 50% RH | 35° C., 50% RH |
| --- | --- | --- | --- |
| 0 ml | 9.5 | 9.5 | 8.0 |
| 0.1 ml | 39.4 | 40.5 | 38.0 |
| 0.5 ml | 106.9 | 109.5 | 48.0 |

$\delta_+$ may also be used as a threshold for determining whether load conditioning should be performed or a sterilization cycle canceled when calculated from pressures measured within a vacuum chamber while the pressure is being decreased from approximately 30 torr to approximately 4.6 torr. Recall that in this pressure range increases in pressure indicate the presence of water and that the water was disposed on a metallic surface. Values of $\delta_+$ were determined experimentally, using techniques similar to those described above for pressures between approximately 4.6 torr and approximately 800 mtorr. For $\delta_+$ greater than 40 mTorr/s$^2$, there may have been at least 1.5 ml of water disposed on a metallic surface in the vacuum chamber. Accordingly for $\delta_+$ greater than 40 mTorr/s$^2$, it may be advisable to abort the sterilization cycle so that healthcare personnel may manually dry the load. Alternatively, because the water is disposed on a metallic surface, load-conditioning may be attempted. However, for $\delta_+$ less than 40 mTorr/s$^2$, $\delta_+$ may not be a reliable indicator of whether or how much water was in the vacuum chamber because water may be disposed on non-metallic surfaces, and therefore, may not be readily vaporized. Accordingly, when $\delta_+$ is less than 40 mTorr/s$^2$ for pressures between approximately 30 torr and approximately 4.6 torr, it may be preferable to allow the sterilization system to determine values of $\delta_+$ for pressures less than approximately 4.6 torr, and to base a determination thereon of whether to sterilize, load condition, or abort the cycle.

IV. Sterilization System Routines

A low-temperature chemical sterilization system, such as sterilization system 10, may be designed to perform various routines concerning determining whether any water is in vacuum chamber 12 and whether the sterilization system may be able to remove water from the vacuum chamber. Example sterilization processes, which include steps that a sterilization system may perform, such as a routine for determining whether load conditioning should be performed, a load conditioning routine, and a sterilization routine, as well as other steps that a healthcare worker may perform, are set forth in FIGS. 5 and 6. These processes are set forth only as examples to further illustrate the disclosed subject matter and explain its utility. Many of the steps included in these processes may be performed alternatively or additionally before or after other steps. The steps set forth in these examples may be performed in varying combinations and permutations without departing from the scope of the disclosed subject matter. For example, load conditioning routines may be performed and/or air plasma introduced into the vacuum chamber before any sterilant is introduced into the vacuum chamber.

Figure 5:
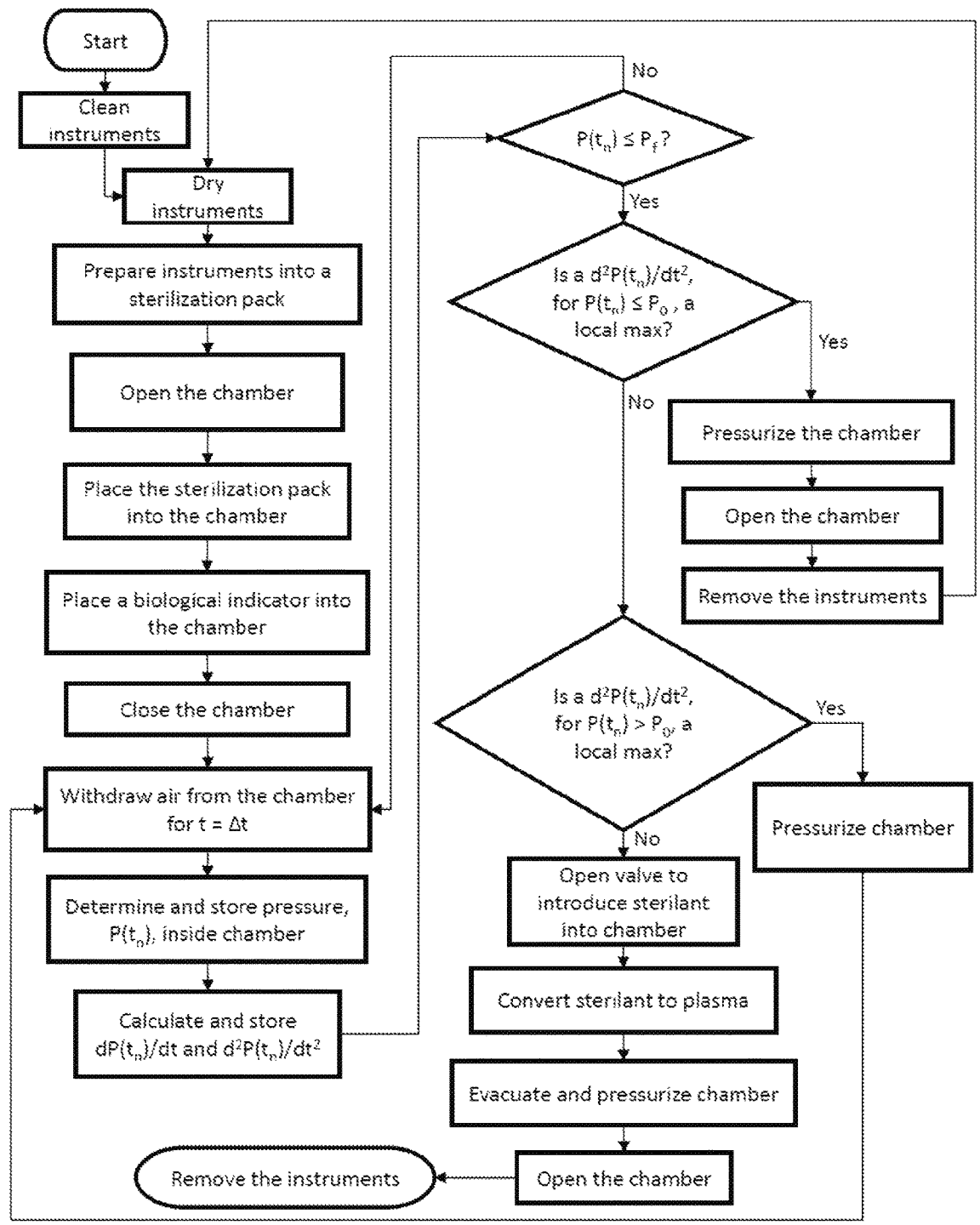
FIG. 5 is a flow diagram of a first exemplary method for using a sterilization system.

As detailed in FIG. 5, one example sterilization process begins with health care personnel cleaning instruments soiled from prior use, using water, washing solution, or a water-soluble instrument lubricant. The instruments are then dried using any or a combination of various techniques known in the art, such as heating the instruments or blowing compressed air into the instruments, particularly lumens of the instrument. The dried instruments may be placed within a sterilization box or rack made from, e.g., a metal, such as aluminum, or a plastic, such as polycarbonate. The instruments and/or rack are wrapped within a sterilization wrap to form sterilization pack or load 14. The wrap acts as a barrier to microorganisms, but it permits passage of a sterilant therethrough. Once wrapped, the pack is ready to be introduced into the vacuum chamber 12 of sterilization system 10.

The openable and sealable barrier 16 of chamber 12 is opened and load 14 is placed therein. A biological indicator may also be placed into the chamber. Then barrier 16 is closed and sealed. The closing and sealing of the chamber via barrier 16 may be accomplished simultaneously or as two separate steps that are conducted in quick succession. The sterilization system begins to evacuate air from within chamber 12 by withdrawing (pumping) air therefrom for a time interval set into the sterilization system by healthcare personnel or the sterilization system's manufacturer. For example, the time interval, $\Delta t$, may be approximately 0.1 second, approximately 1 second, approximately 2 seconds, approximately 5 seconds, or approximately 10 seconds. At the end of the interval, pressure monitor 24 determines the pressure in chamber 12. Control system 38 stores this pressure value $P(t_n)$ in storage medium 42. Next, control system 38 calculates and stores first and second derivatives of pressure with respect to time. However, depending on the manner in which derivatives are numerically calculated, it may be preferred to skip the step of calculating the first and second derivatives until pressures for at least two intervals, i.e., $P(t_n)=\{P(t_0), P(t_1)\}$, three intervals, i.e., $P(t_n)=\{P(t_0), P(t_1), P(t_2)\}$ or more intervals, i.e., $P(t_n)=\{P(t_1), P(t_2), P(t_3), \ldots P(t_m)\}$ have been determined.

Next, control system 38 checks whether the pressure in the chamber has been drawn down to the desired terminal, or final, pressure $P_f$. That is, the system checks whether $P(t_n)$ is less than or equal to $P_f$. To ensure adequate coverage of sterilant gases, it is generally desirable to achieve a $P_f$ of less than or equal to approximately 3 torr, approximately 1 torr, approximately 0.7 torr, approximately 0.5 torr, or approximately 0.3 torr. If control system 38 determines that $P(t_n)$ is greater than $P_f$, control system 38 directs the system to repeat the steps of withdrawing air from vacuum chamber 12, determining $P(t_n)$, storing $P(t_n)$, calculating and storing the first and second derivatives of pressure with respect to time, and determining whether $P(t_n)$ is less than or equal to $P_f$.

Once control system 38 determines that $P(t_n)$ is less than or equal to $P_f$, control system 38 determines whether, for any $P(t_n)$ less than or equal to some threshold pressure, $P_0$, there is a corresponding second derivative value that is a local maximum as among the other second derivative values corresponding to other $P(t_n)$ less than or equal to $P_0$. If control system 38 determines that a local maximum exists in this regime, control system 38 may abort the process. That is, the vacuum chamber 12 is returned to ambient pressure and opened. Then, healthcare personnel may remove the load from chamber 12, and essentially recommence the sterilization process, beginning with drying the instruments. If control system 38 determines that a local maximum does not exist in this regime, control system 38 determines whether there is a $P(t_n)$ greater than $P_0$ that has a corresponding second derivative value that is a local maximum as among the other second derivative values corresponding to other $P(t_n)$ greater than $P_0$.

If control system 38 determines that a local maximum exists where $P(t_n)$ is greater than $P_0$, the sterilization system may conduct load conditioning. Various load-conditioning procedures may be performed. Whatever the procedure, energy is transferred to the residual water because the energy raises the temperature of the water, which helps vaporize the water for subsequent evacuation. Some load-conditioning operations begin before any sterilant gas, e.g., hydrogen peroxide, is evacuated from the chamber. In these operations, the sterilant gas may be converted to a plasma. Following evacuation of chamber 12, chamber 12 may be heated by heating element 26. Alternatively, chamber 12 may be pressurized using heated or hot air having a low relative humidity. Additionally, another vacuum may be drawn in chamber 12 and a plasma from another gas, such as an air plasma, may be introduced therein. Air plasmas may also be used to condition a load before any sterilant is introduced to further attempt vaporization of any water that may be in the load. Likewise, a load conditioning cycle may be performed before any sterilant is introduced to the chamber, e.g., by lowering the pressure in vacuum chamber 12 to $P_f$, pressurizing the chamber with ambient air, and again lowering the pressure to $P_f$.

FIG. 5 includes a load-conditioning operation that includes the following steps. Chamber 12 is pressurized to some greater pressure, which may be less than, equal to, or greater than atmospheric pressure. This pressurization may be performed with ambient air, heated air, or a gas with a low water content, such as air with a low relative humidity. Chamber 12 may also be heated with heating elements 26. The energy from the ambient air, heated air, and/or heating elements 26 may warm any remaining residual water. Next, control system 38 directs the system to repeat the steps of withdrawing air from vacuum chamber 12, determining $P(t_n)$, storing $P(t_n)$, calculating and storing the first and second derivatives of pressure with respect to time, and determining whether $P(t_n)$ is less than or equal to $P_f$. The combination of providing energy to the residual water in combination with lowering the pressure in chamber 12 by removing the air and/or other gas therein may fully or partially remove residual water that remained on the load. Again, the second derivatives for pressures above and below $P_0$ are checked for local maxima to determine if the load is sufficiently dry for introducing the sterilant into the chamber, or if another round of load conditioning may be preferred. Load conditioning may be repeated either until no local maximums are calculated or until the control system 38 times out.

Because it is desirable to determine whether ice crystals may have formed before attempting to condition a load, an exemplary value of $P_0$ may be the triple-point pressure of water, i.e., 4.58 torr. However, it may be desirable to utilize a $P_0$ of between approximately 4 torr and approximately 5 torr. For example, pressures above the triple-point pressure may provide greater confidence that an attempt to condition a load will be successful.

If control system 38 determines that no local maximum exists where $P(t_n)$ is greater than $P_0$, the sterilization system attempts to sterilize the device by introducing a sterilant gas or liquid, such as hydrogen peroxide, into chamber 12. When hydrogen peroxide liquid is used, it should be introduced into chamber 12 as a vapor or in a form, such as droplets, that readily vaporizes. The hydrogen peroxide may also be converted to plasma, which may further improve the sterilization process. Although not shown in the flow chart, the hydrogen peroxide gas may be evacuated from the chamber and another form of plasma, such as an air plasma, may be introduced into the chamber. Introduction of an air plasma may require first returning the vacuum chamber to ambient or near ambient pressure and subsequently drawing another vacuum suitable for introducing the air plasma. After the load has been exposed to hydrogen peroxide gas, and possibly plasma, for a sufficient amount of time to kill microorganisms that may have been in the load, chamber 12 is again evacuated, and the pressure within chamber 12 is equalized to the ambient pressure. Sterilization system 10 may be opened and the instruments, which should now be sterile, may be removed therefrom.

Figure 6:
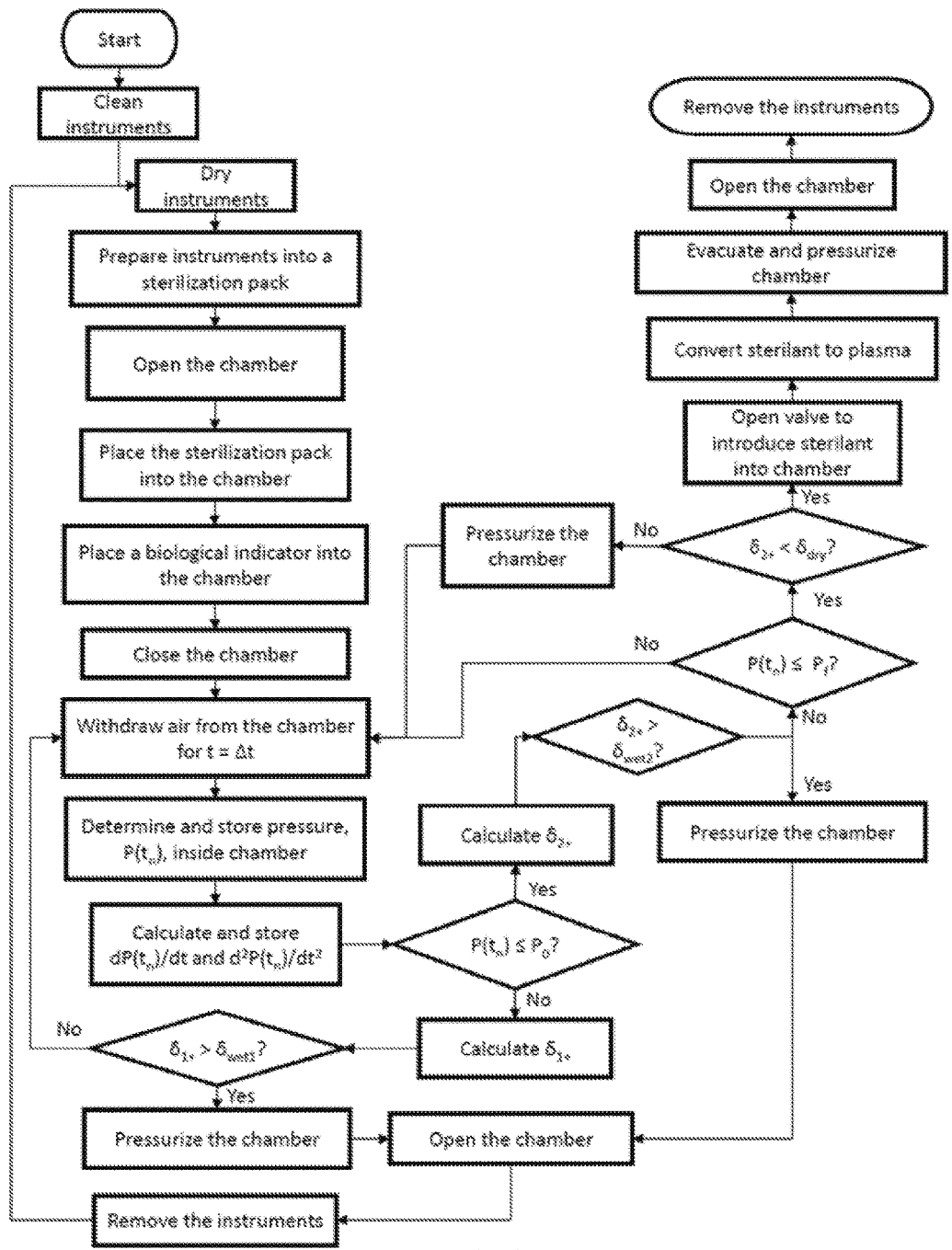
FIG. 6 is a flow diagram of a second exemplary method for using a sterilization system.

Another example sterilization process is set forth in FIG. 6. Like the process described in conjunction with FIG. 5, this process begins with health care personnel cleaning and then drying instruments soiled from prior use, placing the instruments within a sterilization box or rack, wrapping the box or rack to create a sterilization pack or load 14, opening sealable barrier 16 of vacuum chamber 12 of sterilization system 10, placing the load and optionally a biological indicator therein, and closing the chamber. Again, the sterilization system begins to evacuate air from within chamber 12 by withdrawing (pumping) air therefrom for a time interval set into the sterilization system by healthcare personnel or the sterilization system's manufacturer. For example, the time interval, $\Delta t$, may be approximately 0.1 second, approximately 1 second, approximately 2 seconds, approximately 5 seconds, or approximately 10 seconds. At the end of the interval, pressure monitor 18 determines the pressure in chamber 12. Control system 38 stores this pressure value in storage medium 42. Next, control system 38 calculates and stores first and second derivatives of pressure with respect to time. However, depending on the manner in which derivatives are numerically calculated, it may be preferred to skip the step of calculating the first and second derivatives until pressures for at least the first two intervals, i.e., $P(t_n)=\{P(t_0), P(t_1)\}$, first three intervals, i.e., $P(t_n)=\{P(t_0), P(t_1), P(t_2)\}$ or first other number of intervals, i.e., $P(t_n)=\{P(t_1), P(t_2), P(t_3), \ldots P(t_m)\}$ have been determined.

Next, control system 38 determines whether the pressure within chamber 12, $P(t_n)$, is above or below the threshold pressure $P_0$, which may be approximately equal to the triple-point pressure of water. If $P(t_n)$ is greater than $P_0$, control system 38 calculates $\delta_+$, the net positive change to the second derivative of pressure with respect to time over a duration equaling $t_n$. In FIG. 6, $\delta_+$ for $P(t_n)>P_0$ is referred to as $\delta_{1+}$. If $\delta_{1+}$ is greater than a predetermined threshold value determined to correspond to a load that is too wet to be sterilized, $\delta_{wet1}$, then the sterilization process is aborted. In that case, chamber 12 is pressurized and opened so that healthcare personnel may remove the load and dry the instruments before restarting the process. If $\delta_{1+}$ is less than $\delta_{wet1}$, air is withdrawn from the chamber for the subsequent time interval. The foregoing steps of withdrawing air, determining and storing pressure, calculating the first and second derivatives, and calculating $\delta_{1+}$ are repeated until either $\delta_{1+}$ is greater than $\delta_{wet1}$, in which case the process is aborted, or until $P(t_n)$ is less than $P_0$.

The time at which $P(t_n)$ becomes less than $P_0$ may be referred to as $t_{P0}$. At this time, control system 38 begins calculating $\delta_+$ for pressures less than $P_0$, referred to in FIG. 6 as $\delta_{2+}$. That is, $\delta_{2+}$ is the positive change to the second derivative of pressure with respect to time from $t_{P0}$ to $t_n$. If $\delta_{2+}$ is greater than a predetermined threshold value determined to correspond to a load that is too wet to be sterilized, $\delta_{wet2}$, then the sterilization process is aborted. In that case chamber 12 is pressurized and opened so that healthcare personnel may remove the load and dry the instruments before restarting the process. If $\delta_{2+}$ is less than $\delta_{wet2}$, air is withdrawn from the chamber for the subsequent time interval and $\delta_{2+}$ is recalculated for another comparison to $\delta_{wet2}$. These steps repeat until the pressure $P(t_n)$ in chamber 12 has been drawn down to the desired terminal, or final, pressure $P_f$. That is, control system 38 checks whether $P(t_n)$ is less than or equal to $P_f$. To ensure adequate coverage of sterilant gases, it is generally desirable to achieve a $P_f$ of less than or equal to approximately 3 torr, approximately 1 torr, approximately 0.7 torr, approximately 0.5 torr, or approximately 0.3 torr.

Once $P(t_n)<P_f$, control system 38 optionally checks whether $\delta_{2+}$ is greater or less than $\delta_{dry}$, a predetermined threshold value determined to correspond to a load that is dry, and therefore, ready for sterilization. Alternatively, this step may be bypassed. If $\delta_{2+}$ is less than $\delta_{dry}$, or if the step is bypassed, the sterilization system attempts to sterilize the device by introducing a sterilant gas or liquid, such as hydrogen peroxide, into chamber 12. When hydrogen peroxide liquid is used, it should be introduced into chamber 12 as a vapor or in a form, such as droplets, that readily vaporizes. The hydrogen peroxide may also be converted to plasma, which may further improve the sterilization process. Although not shown in the flow chart, the hydrogen peroxide gas may be evacuated from the chamber and another form of plasma, such as an air plasma, may be introduced into the chamber. Introduction of an air plasma may require first returning the vacuum chamber to ambient or near ambient pressure and subsequently drawing another vacuum suitable for introducing the air plasma. After the load has been exposed to hydrogen peroxide gas, and possibly plasma, for a sufficient amount of time to kill microorganisms that may have been in the load, chamber 12 is again evacuated (e.g., vented to atmosphere), and the pressure within chamber 12 is equalized to the ambient pressure. Sterilization system 10 may be opened and the instruments, which should now be sterile, may be removed therefrom.

If, however, the system checks $\delta_{2+}$ against $\delta_{dry}$ and determines that $\delta_{2+}$ is greater than $\delta_{dry}$, a load-conditioning routine may be performed. First, chamber 12 is pressurized. This pressurization may be performed with ambient air, heated air, or a gas with a low water content, such as air with a low relative humidity. Chamber 12 may also be heated with heating elements 60. The energy from the ambient air, heated air, and/or heating elements 26 may warm any remaining residual water. Next, the system repeats the steps of withdrawing air from vacuum chamber 12, determining $P(t_n)$, storing $P(t_n)$, calculating and storing the first and second derivatives of pressure with respect to time, and determining whether $P(t_n)$ is less than or equal to $P_0$ and ultimately less than or equal to $P_f$. The combination of providing energy to the residual water and lowering the pressure in chamber 12 by removing the air and/or other gas therein may fully or partially remove residual water that remained on the load. During load conditioning, $\delta_{1+}$ and $\delta_{2+}$ are compared to their respective wetness thresholds $\delta_{wet1}$ and $\delta_{wet2}$ to confirm the sterilization process should not be aborted. Once $P(t_n)$ is less than or equal to $P_f$, $\delta_{2+}$ is compared to $\delta_{dry}$ to determine whether the load is sufficiently dry for sterilization. Load conditioning may be repeated either until $\delta_{2+}$ is less than $\delta_{dry}$ or until the control system 38 times out.

V. User Feedback

Loads should always be completely dry when they are exposed to a chemical sterilant, such as hydrogen peroxide. Unfortunately, this is not always the case. Healthcare workers sometimes fail to sufficiently and/or properly dry the instruments that are to be sterilized. The heretofore described steps and methods for determining whether any residual water is within a load may also be used to generate user feedback, which may assist healthcare facilities and personnel in drying instruments and loads. For example, the sterilization system may include a user feedback system, including, e.g., control system 38 and a graphical interface that is capable of advising healthcare personnel to remove a load and dry it manually because, e.g., sufficiently large volumes of residual water were detected. The feedback system may display different messages corresponding to the volumes of water detected. For example, if no water is detected, the graphical interface may display a message stating, e.g., "No water detected, sterilization ok." For example, if approximately 1 ml of water is detected, the graphical interface may display a message stating, e.g., "Some water detected, sterilization may be ineffective." For example, if greater than 1.5 ml of water is detected, the graphical interface may display a message stating, e.g., "Unable to condition the load, please remove load and dry."

The system may also compile data for healthcare personnel and managers, which may help identify certain types of loads that are challenging to dry or healthcare personnel that habitually fail to sufficiently dry instruments. The system may store the second derivative and/or $\delta_+$ calculations as well as user information concerning who dried instruments in preparation for sterilization. These calculations may be used to generate statistics for the users of the sterilization system. For example, the system may be able to provide information concerning the percentage of loads that a user completely dried, mostly dried, and/or failed to dry.

Consider a hospital where two nurses, Nurse A and Nurse B, are responsible for sterilizing instruments, including the steps of cleaning, drying, preparing the instruments into loads, and placing the loads into the vacuum chamber of the sterilization system. Over a desired period of time, e.g., each month, the system may generate a report for the hospital's management concerning the dryness of each of the loads Nurse A and Nurse B prepared. For example, the report may indicate that 95% of Nurse A's loads are dry and the other 5% are mostly dry, but that 60% of Nurse B's loads are dry, 20% are mostly dry, and 20% are too wet for sterilization. Based on this information, it would appear that Nurse A achieves better drying results than Nurse B. Accordingly, management may decide to take remedial action toward Nurse B, such as sending him or her for training on how to prepare instruments for sterilization.

It should be understood that any of the examples and/or embodiments described herein may include various other features and/or steps in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A method of operating a sterilization system having a vacuum chamber for sterilizing instruments, comprising:
    (a) initiating a timer in a digital computer;
    (b) withdrawing a first volume of air from the chamber;
    (c) repeatedly determining pressure within the chamber while withdrawing the first volume of air from the chamber;
    (d) calculating, with the digital computer, a first second-derivative value of pressure with respect to time;

(e) calculating, with the digital computer, a second second-derivative value of pressure with respect to time, the second second-derivative value corresponding to a time subsequent to the time corresponding to the first second-derivative value;
(f) determining, with the digital computer, that the second second-derivative value is greater than the first second-derivative value; and
(g) in response to determining that the second second-derivative value is greater than the first second-derivative value, automatically introducing a second volume of air into the chamber.

2. The method of claim 1 wherein the step of repeatedly determining the pressure includes repeatedly taking pressure measurement data and storing the data in a non-transitory storage medium of the digital computer.

3. The method of claim 2 further comprising determining, with the digital computer, that the second second-derivative value occurs at a pressure less than approximately the triple-point pressure of water.

4. The method of claim 3, wherein the step of automatically introducing air into the chamber includes automatically opening a valve.

5. The method of claim 4 further comprising automatically opening the chamber after completing the step of automatically introducing the second volume of air into the chamber.

6. The method of claim 5 further comprising closing the chamber, wherein the step of initiating the timer occurs after the step of closing of the chamber.

7. The method of claim 6 wherein the step of withdrawing a first volume of air from the chamber begins after the step of initiating the timer.

8. The method of claim 7 wherein no sterilant is introduced into the vacuum chamber.

9. The method of claim 1 further comprising the step of determining that the difference between the second second-derivative value and the first second-derivative value is greater than a noise floor.

10. A method of operating a sterilization system having vacuum chamber for sterilizing instruments, comprising:
(a) initiating a timer in a digital computer;
(b) withdrawing a first volume of air from the chamber;
(c) repeatedly determining pressure within the chamber while withdrawing the first volume of air from the chamber;
(d) calculating, with the digital computer, a first second-derivative value of pressure with respect to time;
(e) calculating, with the digital computer, a second second-derivative value of pressure with respect to time, the second second-derivative value corresponding to a time subsequent to the time corresponding to the first second-derivative value;
(f) determining, with the digital computer, that the second second-derivative value is greater than the first second-derivative value; and
(g) in response to determining that the second second-derivative value is greater than the first second-derivative value, automatically introducing energy into the chamber.

11. The method of claim 10 wherein the step of repeatedly determining the pressure includes repeatedly taking pressure measurement data and storing the data in a non-transitory storage medium of the digital computer.

12. The method of claim 11 further comprising determining, with the digital computer, that the second second-derivative value occurs at a pressure greater than approximately the triple-point pressure of water.

13. The method of claim 12 wherein the step of introducing energy to the chamber includes at least one of automatically heating the chamber, automatically opening a valve to introduce air into the chamber that is warmer than the chamber, and automatically generating a plasma.

14. The method of claim 13 further comprising closing the chamber, wherein the step of initiating the timer occurs after the step of closing of the chamber.

15. The method of claim 14 wherein the step of withdrawing the first volume of air from the chamber begins after the step of initiating the timer.

16. A method of operating a sterilization system having vacuum chamber for sterilizing instruments, comprising:
(a) initiating a timer in a digital computer;
(b) withdrawing a first volume of air from the chamber;
(c) repeatedly determining pressure within the chamber while withdrawing the first volume of air from the chamber;
(d) calculating, with the digital computer, a first second-derivative value of pressure with respect to time;
(e) calculating, with the digital computer, a second second-derivative value of pressure with respect to time, the second second-derivative value corresponding to a time subsequent to the time corresponding to the first second-derivative value;
(f) determining, with the digital computer, that the second second-derivative value is less than the first second-derivative value; and
(g) in response to determining that the second second-derivative value is less than the first second-derivative value, automatically introducing a sterilant gas into the chamber.

17. The method of claim 16 wherein the step of repeatedly determining the pressure includes repeatedly taking pressure measurement data and providing the data to a non-transitory storage medium of the digital computer.

18. The method of claim 17 further comprising maintaining a sterilization-appropriate pressure within the chamber.

19. The method of claim 18 wherein the sterilization-appropriate pressure is maintained for at least one second.

20. The method of claim 19 wherein the sterilization-appropriate pressure is between approximately 4 torr and approximately 0.1 torr.

21. The method of claim 20 wherein the sterilization-appropriate pressure is approximately 0.3 torr.

22. The method of claim 19 wherein the step of automatically introducing the sterilant gas into the chamber occurs after the step of maintaining the sterilization-appropriate pressure for at least one second.

23. The method of claim 22 wherein the step of automatically introducing the sterilant gas into the chamber includes opening a valve.

24. The method of claim 23 further including a step of placing the instruments in a non-sterile state into the chamber and closing the chamber before the step of withdrawing the first volume of air from the chamber.

25. The method of claim 24 further comprising opening the chamber and removing the instruments in a sterile-state from the chamber.

26. A method of operating a sterilization system having a vacuum chamber for sterilizing instruments, comprising:
(a) initiating a timer in a digital computer;
(b) withdrawing a first volume of air from the chamber;

(c) repeatedly determining pressure within the chamber while withdrawing the first volume of air from the chamber;

(d) calculating, with the digital computer, second-derivative values of pressure with respect to time;

(e) calculating, with the digital computer, a summation of positive differences between consecutive second derivative values;

(f) comparing the summation to a threshold value;

(g) determining that the summation is greater than the threshold value; and (h) in response to determining that the summation is greater than the threshold value, opening a valve to cause the pressure in the chamber to increase.

27. The method of claim 26 wherein the pressure in the chamber is increased by a second volume of air flowing past the valve and into the chamber.

28. The method of claim 27, wherein the second volume of air flowing into the chamber vaporizes a volume of water.

29. A method of operating a sterilization system having a vacuum chamber for sterilizing instruments, comprising:

(a) initiating a timer in a digital computer;

(b) withdrawing a first volume of air from the chamber;

(c) repeatedly determining pressure within the chamber while withdrawing the first volume of air from the chamber;

(d) calculating, with the digital computer, second-derivative values of pressure with respect to time;

(e) calculating, with the digital computer, a summation of positive differences between consecutive second derivative values;

(f) comparing the summation to a threshold value;

(g) determining that the summation is less than the threshold value; and (h) in response to determining that the summation is less than the threshold value, introducing a sterilant into the chamber.

30. The method of claim 29 wherein the summation is a first summation that is terminated when a difference between consecutive second derivative values is negative.

31. The method of claim 30 wherein a second summation is commenced after the first summation is terminated when a difference between consecutive second derivative values is positive.

* * * * *